United States Patent [19]
Gildert et al.

[11] Patent Number: 5,773,670
[45] Date of Patent: Jun. 30, 1998

[54] HYDROGENATION OF UNSATURATED CYCLIC COMPOUNDS

[76] Inventors: Gary R. Gildert; Dennis Hearn; Hugh M. Putman, all of 10100 Bay Area Blvd., Pasadena, Tex. 77507

[21] Appl. No.: 398,690

[22] Filed: Mar. 6, 1995

[51] Int. Cl.$^6$ .................................................. C07C 5/10
[52] U.S. Cl. ................................ 585/266; 203/DIG. 6; 585/250
[58] Field of Search ................................ 585/266, 250; 203/DIG. 6

[56] References Cited

U.S. PATENT DOCUMENTS

| | | | |
|---|---|---|---|
| 2,373,501 | 4/1945 | Peterson | 260/667 |
| 3,450,784 | 6/1969 | Reilly et al. | 260/667 |
| 3,912,787 | 10/1975 | Nowack et al. | 260/667 |
| 3,931,345 | 1/1976 | Gryaznov et al. | 260/667 |
| 4,108,912 | 8/1978 | Takemura et al. | 260/667 |
| 4,115,462 | 9/1978 | Thelen et al. | 260/667 |
| 4,197,415 | 4/1980 | Hideyuki et al. | 585/23 |
| 4,225,418 | 9/1980 | Hilfman | 208/111 |
| 4,228,312 | 10/1980 | Noltes et al. | 585/250 |
| 4,232,177 | 11/1980 | Smith | 585/324 |
| 4,327,234 | 4/1982 | Nowack et al. | 585/267 |
| 4,409,411 | 10/1983 | Pez | 585/275 |
| 4,731,496 | 3/1988 | Hu et al. | 585/270 |
| 5,003,118 | 3/1991 | Low et al. | 585/253 |
| 5,087,780 | 2/1992 | Arganbright | 585/259 |
| 5,189,233 | 2/1993 | Larkin et al. | 585/265 |
| 5,210,333 | 5/1993 | Bellows et al. | 585/827 |
| 5,210,348 | 5/1993 | Hsieh et al. | 585/253 |
| 5,246,567 | 9/1993 | Buttke et al. | 208/49 |
| 5,254,763 | 10/1993 | Gill et al. | 585/269 |
| 5,264,641 | 11/1993 | Borghard et al. | 585/269 |
| 5,266,546 | 11/1993 | Hearn | 502/300 |

FOREIGN PATENT DOCUMENTS 0552070 7/1993 European Pat. Off. .

*Primary Examiner*—Glenn A. Caldarola
*Assistant Examiner*—Bekir L. Yildirim
*Attorney, Agent, or Firm*—Kenneth H. Johnson

[57] ABSTRACT

A process for the hydrogenation of unsaturated cyclic and polycyclic compounds to saturates is provided wherein the reactor is operated at a pressure wherein the reaction mixture is boiling under low hydrogen partial pressure in the range of about 0.1 psi to less than 70 psia at 0 to 350 psig. The catalyst is provided as a catalytic distillation structure such that the reaction is concurrently occurring with a distillation. A portion of the overheads is returned as reflux to provide cooling within the catalyst bed and concurrent condensation of some of the gaseous material within the bed. Although no separation is obtained all of the advantages of concurrent reaction with distillation are achieved.

18 Claims, 1 Drawing Sheet

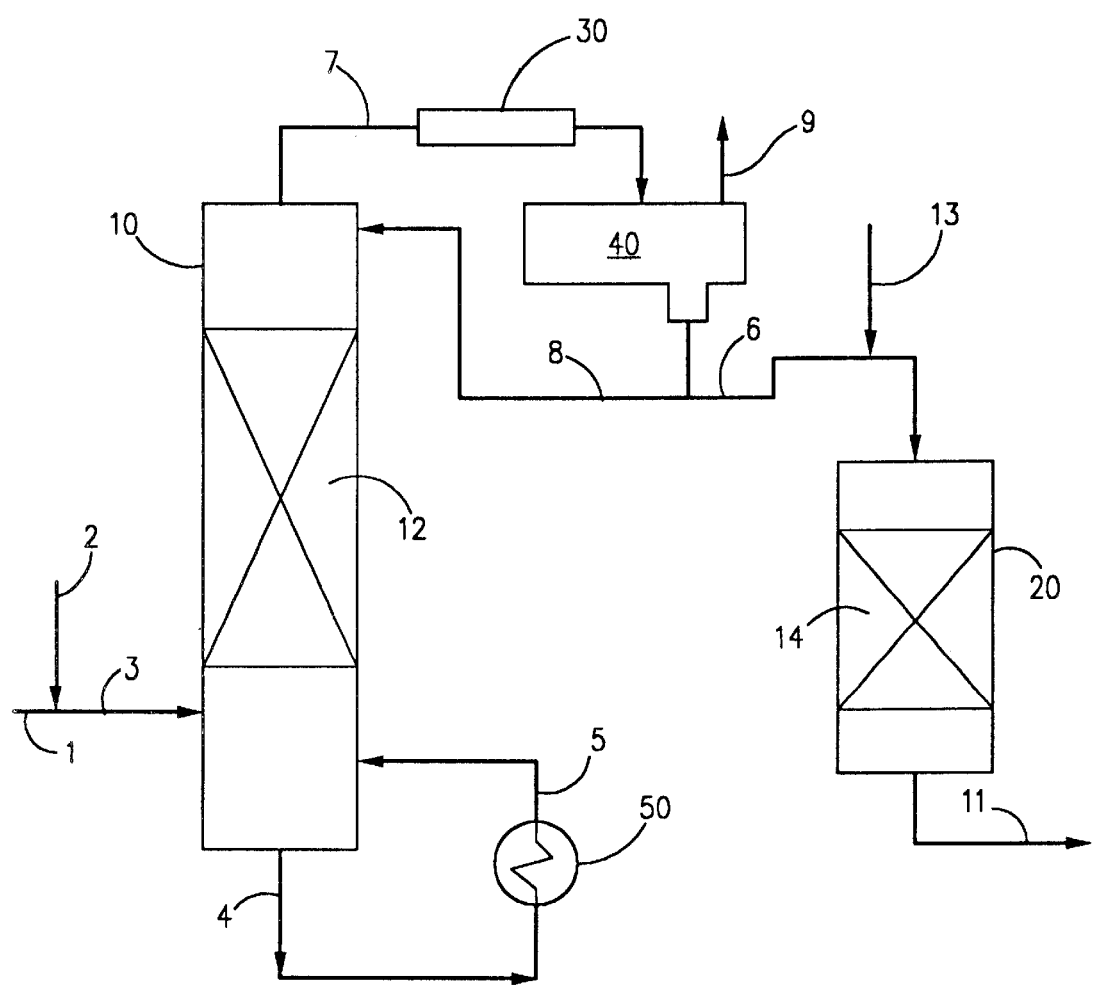

HYDROGENATION OF UNSATURATED CYCLIC COMPOUNDS

BACKGROUND OF THE INVENTION

1. Field of the Invention

The present invention relates to the hydrogenation of unsaturated cyclic and polycyclic compounds. More particularly the invention relates to a process wherein the hydrogenation of the unsaturated cyclic and polycyclic compounds and separation of the product by distillation is carried out simultaneously in a distillation column reactor. More particularly the process relates to the hydrogenation of benzene to make cyclohexane.

2. Related Information

Cyclohexane is the main precursor for the production of nylon products and as such the demand remains strong. Cyclohexane was first obtained by the direct fractional distillation of suitable crude petroleum refinery streams. Now the major portion of cyclohexane is obtained from the direct hydrogenation of benzene.

Peterson in U.S. Pat. No. 2,373,501 discloses a liquid phase process for the hydrogenation of benzene to cyclohexane wherein a temperature differential is maintained between the top of the catalyst bed where benzene is fed and the outlet where substantially pure cyclohexane is withdrawn. The temperature differential is due to the change in the exothermic heat of reaction released as less and less benzene is converted as the concentration of benzene decreases. Hydrogen is supplied counter current to the benzene/cyclohexane flow. Temperature control coils are disposed within the reactor to maintain the temperature differential if the exothermic heat of reaction is not sufficient or to cool the bed if too much heat is released. Peterson recognizes that although the bulk of his reaction takes place in the liquid phase a portion of the benzene and cyclohexane will be vaporized, especially near the top of the reactor where the benzene concentration is highest and conversion is highest. A reflux condenser is provided to condense the condensible material and return it to the reactor. Thus a substantial portion of the heat of reaction is removed by condensation of the reactants vaporized throughout the reaction.

Larkin, et al. in U.S. Pat. No. 5,189,233 disclose another liquid phase process for the hydrogenation of benzene to cyclohexane. However, Larkin, et al utilize high pressure (2500 psig) to maintain the reactants in the liquid state. In addition Larkin, et al disclose the use of progressively more active catalyst as the concentration of benzene decreases to control the temperature and unwanted side reactions.

Hui, et al. in U.S. Pat. No. 4,731,496 disclose a gas phase process for the hydrogenation of benzene to cyclohexane over a specific catalyst. The catalyst reported therein is nickel supported on a mixture of titanium dioxide and zirconium dioxide.

The hydrogenation of benzene is also useful to remove that aromatic compound from gasoline streams. One example of this process is disclosed by Hsieh, et al in U.S. Pat. No. 5,210,348 wherein hydrogenation of the benzene fraction is used alone or in combination with alkylation. In some schemes for the reduction of aromatic compounds in gasoline the ASTM D-86 90% point is specified such that the aromatic and unsaturated cyclic and polycyclic compounds are precluded from the gasoline blending pool. This has been termed a T-90 gasoline stock having a desired ASTM 90% point. The resultant T-90+ bottoms which are largely unsaturated cyclic and polycyclic compounds must be disposed of and hydrogenating them to produce lighter more saturated compounds for the gasoline pool is an attractive alternative.

A typical problem with the hydrogenation of benzene to cyclohexane is the competing reactions. Particularly isomerization to methyl cyclopentane is unwanted. Additionally at higher temperatures cracking of the ring occurs producing undesirable $C_5$ and lighter products.

SUMMARY OF THE INVENTION

The present invention comprises feeding a hydrocarbon stream containing aromatics and other unsaturated cyclic and polycyclic compounds, particularly benzene, along with a hydrogen stream at an effectuating hydrogen partial pressure of at least about 0.1 psia to less than 70 psia, preferably less than 50 psia in the range of 2 to 25 psia to a distillation column reactor containing a hydrogenation catalyst which is a component of a distillation structure and hydrogenating a portion of the aromatics and other unsaturated cyclic and polycyclic compounds.

BRIEF DESCRIPTION OF THE DRAWING

The FIGURE is a flow diagram of one embodiment of the invention.

DETAILED DESCRIPTION OF THE INVENTION

To provide the desired degree of temperature and residence time control a process and apparatus is provided wherein the reaction liquid is boiling within a distillation column reactor. Overheads are withdrawn and condensed with some of the condensate being returned to the distillation column reactor as reflux. The advantage of the present process is that due to the continual reflux a portion of the aromatics and other unsaturated cyclic and polycyclic compounds is always condensing on the catalyst structure.

Without limiting the scope of the invention it is proposed that the mechanism that produces the effectiveness of the present process is the condensation of a portion of the vapors in the reaction system, which occludes sufficient hydrogen in the condensed liquid to obtain the requisite intimate contact between the hydrogen and the benzene in the presence of the catalyst to result in their hydrogenation. Additionally, the vaporization of the liquid feed removes a substantial amount of the exothermic heat of reaction. Since the liquid is at the boiling point in the reactor, the temperature may be controlled by the pressure. An increase in pressure increases the temperature and a decrease in pressure decreases the temperature.

The terms "cyclic" and "polycyclic" compounds used herein include organic compounds of 2–50 carbon atoms and oxygen, nitrogen sulfur and combinations thereof.

A preferred class comprising structure of the formula:

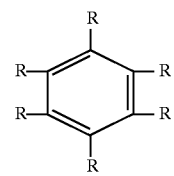

wherein each R is independently selected from hydrogen, alkyl, alkenyl, alkylaryl, saturated and unsaturated cyclic structures formed by two R, containing C, O, N, S, or combinations thereof.

Some specific compounds include benzene, toluene, xylene, ethyl benzene, diethylbenzene, cumene, diisopylbenzene, phenol, durene, pentamethylbenzene, naphthalene, 1,2,3,4-tetrahydronapthalene, 1-methylnaphthalene, diphenylmethane, 2,2+,3,3',4,4',5,5', 6-nonomethyldiphenylmethane, hexamethylbenzene, 1,2,4, 5,6,8-hexamethylanthracene, pentamethylphenol, durenol, mesitol, methyldiphenylmethane, pentamethylphenol, 1,1-binaphthyl, 1,2,3,4-tetrahydronaphthalene (tetralin), 4,4'-dimethyl-1,1'-binaphthyl, triphenylmethane, p-dibenzylbenzene, tetramethyldiphenylmethane, furan, thiophene, pyrrole, isopyrrole, pyrazole, 2-isoimidazole, 1,2,4-triazole, 1,2-dithiole, 1,2,3-oxyathiole, thiazole, 1,2-pyran, 1,4-pyrone, 1,2-dioxin, pyridine, triazive, 1,3,2-oxazine, 1,2,5-oxathiazine, azepine, indene, benzofurane, indole, benzoxazole, coumarin, quinayoline, phenanthrene, benzonaphthene, fluorene, xanthene, acridine, perylene, terpenes and naphthenes.

The present hydrogenations may be carried out to produce totally saturated compounds corresponding to the starting material or in some instances compounds having reduced unsaturation from the starting material. Not uncommonly the hydrogenation results in the cession of the ring structure and some cracking.

The hydrogenations described herein are exothermic reactions. In the past the temperature has been controlled by quench at strategic points within a reactor by addition of cool hydrogen. The addition of the hydrogen also acted to maintain a molar excess of hydrogen within the reactor to prevent coking and other undesirable side reactions. It is believed that in the present reaction catalytic distillation is a benefit first, because the reaction is occurring concurrently with distillation, the initial reaction products and other stream components are removed from the reaction zone as quickly as possible reducing the likelihood of side reactions. Second, because all the components are boiling the temperature of reaction is controlled by the boiling point of the mixture at the system pressure. The heat of reaction simply creates more boil up, but no increase in temperature at a given pressure.

The present invention carries out the method in a catalyst packed column which can be appreciated to contain a vapor phase and some liquid phase as in any distillation. The distillation column reactor is operated at a pressure such that the reaction mixture is boiling in the bed of catalyst. The present process for hydrogenating benzene operates at overhead pressure of said distillation column reactor in the range between 0 and 350 psig, preferably 250 or less suitable 35 to 120 psig and temperatures in said distillation reaction bottoms zone in the range of 100° to 500° F., preferably 150° to 400° F., e. g. 212° to 374° F. at the requisite hydrogen partial pressures. The feed weight hourly space velocity (WHSV), which is herein understood to mean the unit weight of feed per hour entering the reaction distillation column per unit weight of catalyst in the catalytic distillation structures, may vary over a very wide range within the other condition perimeters, e.g. 0.1 to 35. Hydrogenation conditions used for other unsaturated cyclic and polycyclic compounds are similar to those for benzene, although some of the compounds may require higher temperatures to volatilize the materials of the process.

In the current process the temperature is controlled by operating the reactor at a given pressure to allow partial vaporization of the reaction mixture. The exothermic heat of reaction is thus dissipated by the latent heat of vaporization of the mixture. The vaporized portion is taken as overheads and the condensible material condensed and returned to the column as reflux.

The downward flowing liquid causes additional condensation within the reactor as is normal in any distillation. The contact of the condensing liquid within the column provides excellent mass transfer for dissolving the hydrogen within the reaction liquid and concurrent transfer of the reaction mixture to the catalytic sites. It is thought that this condensing mode of operation results in the excellent conversion and selectivity of the instant process and allows operation at the lower hydrogen partial pressures and reactor temperatures noted. A further benefit that this reaction may gain from catalytic distillation is the washing effect that the internal reflux provides to the catalyst thereby reducing polymer build up and coking. Internal reflux may vary over the range of 0.2 to 20 L/D (wt. liquid just below the catalyst bed/wt. distillate) give excellent results.

The catalyst is prepared in the form of a catalytic distillation structure. More particularly the hydrogenation catalyst is generally a metal supported on an alumina carrier in the form of extrudates or spheres. The extrudates or spheres are placed in porous containers and suitably supported in the distillation column reactor to allow vapor flow through the bed, yet provide a sufficient surface area for catalytic contact.

Among the metals known to catalyze the hydrogenation reaction are platinum, rhenium, cobalt, molybdenum, nickel, tungsten and palladium. Generally, commercial forms of catalyst use supported oxides of these metals. The oxide is reduced to the active form either prior to use with a reducing agent or during use by the hydrogen in the feed. These metals also catalyze other reactions, most notably dehydrogenation at elevated temperatures. Additionally they can promote the reaction of olefinic compounds with themselves or other olefins to produce dimers or oligomers as residence time is increased.

One preferred embodiment is for the production of cyclohexane from the hydrogenation of benzene. When cyclohexane is the product the benzene containing feed is characterized as preferably containing at least 5 wt % benzene up to 100 wt %. Other components are typically $C_5$, $C_6$ and $C_7$ hydrocarbons. Since other unsaturated compounds may be hydrogenated, the presence of these compounds are detrimental to the process when cyclohexane is the desire product. Preferably other unsaturated compounds should be limited to less than 30% of the feed. Cyclohexane is the preferred diluent, since it is the desired product. However, other inerts such as other alkanes are acceptable, such as $C_5$'s up to $C_9$'s.

The mole ratio of hydrogen to benzene fed to the distillation column reactor is preferably between 1.5:1 and 41:1.

As described the catalytic material employed in the hydrogenation process is in a form to serve as distillation packing. Broadly stated, the catalytic material is a component of a distillation system functioning as both a catalyst and distillation packing, i.e., a packing for a distillation column having both a distillation function and a catalytic function.

The reaction system can be described as heterogenous since the catalyst remains a distinct entity. Any suitable hydrogenation catalyst may be used, for example Group VIII metals of the Periodic Table of Elements as the principal catalytic component, alone or with promoters and modifiers such as palladium/gold, palladium/silver, cobalt/zirconium, nickel preferably deposited on a support such as alumina, fire brick, pumice, carbon, silica, resin or the like.

A preferred catalyst structure for the hydrogenation of benzene comprises at least one plurality of flexible, semi-rigid open mesh tubular elements filled with a particulate catalytic material (catalyst component) and sealed at both ends, intimately associated with and supported by a wire mesh screen coiled into a spiral having a longitudinal axis, said tubular element being arrayed at an angle to the longitudinal axis thereby forming a bale and is described in detail in U.S. patent application Ser. No. 08/188,803 filed Jan. 31, 1994 incorporated herein.

The flexible, semi-rigid open mesh tubular element filed with a particulate catalytic material preferably has a fastener every 1–12 inches along the length of the tube to form a multiple link shaped catalytic distillation structure. The links formed by the fasteners may be evenly or irregularly spaced.

The bale shaped catalytic distillation structures are formed by placing at least one tubular element on top of the wire mesh screen, such as demister wire, in a diagonal array, such that when the wire mesh screen is rolled up, the rolled structure provides a new and improved catalytic distillation structure. Further embodiments include multiple stack arrangements of alternating wire screen mesh and tubular elements that are rolled into a new bale shaped catalytic distillation structure. The tubular elements on alternating layers are preferably arrayed on the wire mesh screen in opposite directions such that their paths cross. Each tubular element will define a spiral within the bale.

The catalyst component may take several forms. In the case of particulate catalytic material, generally from 60 mm to about 1 mm down through powders, is enclosed in a porous container such as screen wire, or polymeric mesh. The material used to make the container must be inert to the reactants and conditions in the reaction system. The screen wire may be aluminum, steel, stainless steel, and the like. The polymer mesh may be nylon, teflon, or the like. The mesh or threads per inch of the material used to make the container is such that the catalyst is retained therein and will not pass through the openings in the material. Although the catalyst particles of about 0.15 mm size or powders may be used and particles up to about ¼ inch diameter may be employed in the containers.

Referring now to the FIGURE there is shown a flow diagram of the benzene embodiment of the invention. Benzene is fed via line 1 and hydrogen via line 2 both being combined in line 3 which feeds the hydrogen and benzene below the catalytic distillation structure 12 contained in distillation column reactor 10. If desired the benzene feed may be diluted with cyclohexane. Heat necessary for start up and to balance the process is provided by circulating the bottoms stream 4 through reboiler 50 and return line 5. The benzene is boiled up into the bed where a portion reacts with hydrogen to form a reaction mixture containing the reaction product cyclohexane, unreacted benzene and unreacted hydrogen. The exothermic heat of reaction causes more boil up of the reaction mixture with the vaporized portion leaving the column as overheads via flow line 7. Unreacted hydrogen also exits with the overheads. The gaseous overheads containing benzene, cyclohexane and hydrogen are passed through condenser 30 where substantially all of the benzene and cyclohexane are condensed. The overheads stream is then passed to receiver/separator 40 where the gas which is mostly hydrogen is separated and the liquid collected. The gas is removed via line 9 for recycle or use later in the process.

A portion of the condensed liquid is returned to the distillation column as reflux where it provides additional cooling and condensing within the column. The bottoms, containing benzene and cyclohexane, are removed via flow line 4 with a portion being recirculated through reboiler 50 and flow line 5. There is no bottoms product stream taken.

The overheads liquid product stream is finally passed via flow line 6 to single pass fixed bed reactor 20 containing a fixed bed of hydrogenation catalyst 14 where substantially all of the unreacted benzene is hydrogenated to cyclohexane. Hydrogen is provided to second reactor 20 via flow line 13 which may conveniently be taken from the vent 9 of overhead receiver 40 if desired.

The present process allows for the use of much lower hydrogen partial pressures and somewhat lower temperatures than normal processes.

In the following examples a 1 inch diameter distillation column reactor was used. The catalyst structure as described above was placed in the top 13 feet of the reactor. The bottom 7 feet were filled with inert distillation packing. The overhead pressure was set as desired and the reboiler was charged with cyclohexane and heat added. When the desired top to bottom temperature differential was obtained the liquid feed rate was established and hydrogen flow started. After a level was noted in the overhead receiver cyclohexane flow was stopped and the unit operated at total reflux for two hours before the benzene/cyclohexane feed was started. Overheads liquids product draw was set to balance the column.

EXAMPLE 1

400 grams of ¹⁄₁₆ inch spherical alumina supported nickel (54 wt % Ni) catalyst were loaded into the tubular elements and wound into a bale as previously described and placed into the distillation column reactor. Conditions and results are shown in Table I below.

TABLE I

| | | | |
|---|---|---|---|
| Time on stream, hrs | 51 | 134.8 | 219 |
| Pressure, psig | 60 | 35 | 35 |
| Bottoms Temp. °F. | 349 | 212 | 219 |
| Internal Reflux Ratio | 23.3 | 2.5 | 2.5 |
| Feed Rate, lbs/hr liq. | 1 | 1 | 1 |
| H2 Rate scfh, gas | 7.5 | 7.5 | 7.5 |
| H2/Bz mole ratio | 4.2 | 4.2 | 4.2 |
| Benzene in feed, wt % | 36 | 36 | 36 |
| Pressure Drop psi | 3.58 | 3.60 | 3.00 |
| H2 pp, psia | 4.74 | 21.92 | 21.92 |
| overhead anal, wt % | | | |
| Cyclohexane | 77.68 | 82.68 | 91.50 |
| Benzene | 21.75 | 17.22 | 8.50 |

EXAMPLE 2

280 grams of alumina supported platinum/palladium (0.3 wt % Pt, 0.5 wt % Pd) catalyst were loaded into the tubular elements and wound into a bale as described above and placed into the distillation column reactor. Conditions and results are shown in Table II below.

TABLE II

| | | |
|---|---|---|
| Time on stream, hrs | 148 | 346 |
| Pressure, psig | 100 | 120 |
| Bottoms Temp. °F. | 356 | 374 |
| Internal Reflux Ratio | 23.2 | 23.1 |
| Feed Rate, lbs/hr liq. | 1 | 1 |
| H2 Rate scfh, gas | 10.0 | 10.0 |
| Benzene in feed, wt % | 36 | 5 |
| H2/Bz mole ratio | 5.6 | 40.6 |
| Pressure Drop psi | 3.85 | 3.80 |
| H2 pp, psia | 9.72 | 11.52 |

TABLE II-continued

| overhead anal, wt % | | |
|---|---|---|
| Cyclohexane | 76.56 | 99.88 |
| Benzene | 23.4 | 0.067 |

EXAMPLE 3

400 grams of 3/26 inch alumina supported nickel (54 wt % Ni) tablets were loaded into the tubular elements and wound into a bale as described above and placed into the distillation column reactor. Conditions and results are shown in Table III below.

TABLE III

| Time on stream, hrs | 43 | 331 | 493 |
|---|---|---|---|
| Pressure, psig | 60 | 100 | 100 |
| Bottoms Temp. °F. | 316 | 355 | 355 |
| Internal Reflux Ratio | 23.4 | 29.7 | 29.7 |
| Feed Rate, lbs/hr liq. | 2.0 | 2.0 | 2.0 |
| H2 Rate scfh, gas | 7.5 | 7.5 | 10.0 |
| Benzene in feed, wt % | 5.9 | 13.7 | 4.9 |
| H2/Bz mole ratio | 25.9 | 11.1 | 41.5 |
| Pressure Drop psi | 3.81 | 4.22 | 4.00 |
| H2 pp, psia | 2.37 | 2.93 | 3.92 |
| overhead anal, wt % | | | |
| Cyclohexane | 96.57 | 90.06 | 98.91 |
| Benzene | 3.41 | 9.93 | 1.09 |

The preferred embodiment has been shown to be for the hydrogenation of benzene. However, the invention also covers the hydrogenation of any stream containing cyclic and polycyclic unsaturates as a T-90+ gasoline bottoms. Such unsaturates include aromatics, polynuclear aromatics, and cyclic alkenes such as naphthenes.

The invention claimed is:

1. A process for the hydrogenation of unsaturated cyclic compounds comprising the steps of:
    (a) feeding a first stream containing unsaturated cyclic compounds and a second stream containing hydrogen to a distillation column reactor at a mole ratio of hydrogen to unsaturated cyclic compound between 1.5:1 and 41:1;
    (b) contacting the unsaturated cyclic compounds and hydrogen at a temperature in the range of 100° to 374° F., a hydrogen partial pressure of less than 50 psia, and an overhead pressure in the range of 0 to 120 psig in the presence of a bed of hydrogenation catalyst prepared in the form of a catalytic distillation structure thereby reacting a portion of the unsaturated cyclic compounds with a portion of the hydrogen to form a reaction mixture containing saturated cyclic compounds, unreacted hydrogen and unreacted unsaturated cyclic compounds;
    (c) maintaining the pressure in the distillation column reactor (i) to contain a vapor phase and some liquid phase and provide a continual reflux such that the reaction mixture is at its boiling point and boiling in the bed of catalyst and (ii) condensing a portion of the vapors in the reaction system whereby a portion of the aromatics and other unsaturated cyclic and polycyclic compounds is always condensing on the catalyst structure;
    (d) removing gaseous unsaturated cyclic compounds, gaseous saturated cyclic compounds and hydrogen as overheads from the distillation column reactor;
    (e) condensing substantially all of the unsaturated cyclic compounds and saturated cyclic compounds removed as overheads from the distillation column reactor;
    (f) returning a portion of the condensed unsaturated cyclic compounds and saturated cyclic compounds to the distillation column reactor as reflux; and
    (g) withdrawing an overheads liquid product containing saturated cyclic compounds and unreacted unsaturated cyclic compounds from the distillation column.

2. The process according to claim 1 wherein the overhead pressure of the distillation column reactor is between 0 and 350 psig.

3. The process according to claim 1 wherein the hydrogen partial pressure is between 0.1 and 50 psia.

4. The process according to claim 3 wherein the hydrogen partial pressure is between 2 and 25 psia.

5. The process according to claim 1 wherein the overhead pressure of the distillation column reactor is between 35 and 120 psig.

6. The process according to claim 1 wherein said catalytic distillation structure comprises a first plurality of flexible, semi-rigid open mesh tubular elements filled with a particulate hydrogenation catalytic material, sealed at both ends, intimately associated with and supported by a wire mesh screen coiled into a spiral having a longitudinal axis, said tubular elements being arrayed at an angle to the longitudinal axis.

7. A process for the production of cyclohexane from the hydrogenation of benzene comprising the steps of:
    (a) feeding a first stream containing benzene and a second stream containing hydrogen to a distillation column reactor at a mole ratio of hydrogen to benzene between 1.5:1 and 41:1;
    (b) contacting the benzene and hydrogen at a temperature in the range of 100° to 374° F., a hydrogen partial pressure of less than 50 psia and an overhead pressure in the range of 0 to 120 psig in the presence of a hydrogenation catalyst prepared in the form of a catalytic distillation structure thereby reacting a portion of the benzene with a portion of the hydrogen to form a reaction mixture containing cyclohexane, unreacted hydrogen and unreacted benzene;
    (c) maintaining the pressure in the distillation column reactor (i) to contain a vapor phase and some liquid phase and provide a continual reflux such that the reaction mixture is at its boiling point, boiling in the bed of catalyst and (ii) condensing a portion of the vapors in the reaction system whereby a portion of the aromatics and other unsaturated cyclic and polycyclic compounds is always condensing on the catalyst structure;
    (d) removing gaseous benzene, gaseous cyclohexane and hydrogen as overheads from the distillation column reactor;
    (e) condensing substantially all of the benzene and cyclohexane removed as overheads from the distillation column reactor;
    (f) returning a portion of the condensed benzene and cyclohexane to the distillation column reactor as reflux; and
    (g) withdrawing an overheads liquid product containing cyclohexane and unreacted benzene from the distillation column.

8. The process according to claim 7 wherein the overhead pressure is between 0 and 350 psig.

9. The process according to claim 7 wherein the overhead pressure of the distillation column reactor is between 35 and 120 psig.

10. The process according to claim 7 wherein said first stream comprises 5–36 weight percent benzene.

11. The process according to claim 7 wherein the remainder of said first stream comprises cyclohexane.

12. The process according to claim 7 further comprising the step of passing said overheads liquid product containing cyclohexane and unreacted benzene along with hydrogen to a single pass fixed bed reactor containing a hydrogenation catalyst to react substantially all of the unreacted benzene with hydrogen to produce additional cyclohexane.

13. The process according to claim 9 wherein the bottoms temperature of the distillation column reactor is between 212° and 374° F.

14. A process for the production of cyclohexane from the hydrogenation of benzene comprising the steps of:

(a) feeding a first stream containing benzene and a second stream containing hydrogen in a mole ratio of hydrogen to benzene of between 1.5:1 and 41:1 to a distillation column reactor;

(b) contacting the benzene and hydrogen at a temperature in the range of 100° to 374° F. and hydrogen partial pressure between 2 and 25 psia in the presence of a hydrogenation catalyst prepared in the form of a catalytic distillation structure thereby reacting a portion of the benzene with a portion of the hydrogen to form a reaction mixture containing cyclohexane, unreacted hydrogen and unreacted benzene;

(c) maintaining the overhead pressure in the distillation column reactor between 35 and 120 psig (i) to contain a vapor phase and some liquid phase and provide a continual reflux such that the reaction mixture is at its boiling point, boiling in the bed of catalyst and (ii) condensing a portion of the vapors in the reaction system whereby a portion of the aromatics and other unsaturated cyclic and polycyclic compounds is always condensing on the catalyst structure;

(d) removing gaseous benzene, gaseous cyclohexane and hydrogen as overheads from the distillation column reactor;

(e) condensing substantially all of the benzene and cyclohexane removed as overheads from the distillation column reactor;

(f) returning a portion of the condensed benzene and cyclohexane to the distillation column reactor as reflux;

(g) withdrawing an overheads liquid product containing cyclohexane and unreacted benzene from the distillation column; and (h) passing said overheads liquid product containing cyclohexane and unreacted benzene along with hydrogen to a single pass fixed bed reactor containing a hydrogenation catalyst to react substantially all of the unreacted benzene with hydrogen to produce additional cyclohexane.

15. The process according to claim 14 wherein said first stream comprises 5–36 weight percent benzene.

16. The process according to claim 14 wherein said catalytic distillation structure comprises a first plurality of flexible, semi-rigid open mesh tubular elements filled with a particulate hydrogenation catalytic material, sealed at both ends, intimately associated with and supported by a wire mesh screen coiled into a spiral having a longitudinal axis, said tubular elements being arrayed at an angle to the longitudinal axis.

17. The process according to claim 1 wherein said saturated cyclic compound comprises monocyclic compounds.

18. The process according to claim 1 wherein said saturated cyclic compound comprises polycyclic compounds.

* * * * *